United States Patent
Khanuja et al.

(10) Patent No.: US 7,435,877 B2
(45) Date of Patent: Oct. 14, 2008

(54) **DISTINCT TYPE CULTIVAR OF *OCIMUM BASILICUM* "CIM-SAUMYA"**

(75) Inventors: Suman Preet Singh Khanuja, Uttar Pradesh (IN); Raj Kishori Lal, Uttar Pradesh (IN); Arun Kumar Agnihotri, Uttar Pradesh (IN); Ajit Kumar Shasany, Uttar Pradesh (IN); Ali Arif Naqvi, Uttar Pradesh (IN); Samresh Dwivedi, Uttar Pradesh (IN); Hari Om Misra, Uttar Pradesh (IN); Om Prakesh Dhawan, Uttar Pradesh (IN); Alok Kalra, Uttar Pradesh (IN); Aparbal Singh, Uttar Pradesh (IN); Janak Raj Bahl, Uttar Pradesh (IN); Saudan Singh, Uttar Pradesh (IN); Dharani Dhar Patra, Uttar Pradesh (IN); Shilpi Agarwal, Uttar Pradesh (IN); Mahendra Pandurang Darokar, Uttar Pradesh (IN); Anil Kumar Gupta, Uttar Pradesh (IN); Moti Lal Gupta, Uttar Pradesh (IN); Ram Chandra, Uttar Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/913,792

(22) Filed: Aug. 6, 2004

(65) Prior Publication Data
US 2006/0031957 A1    Feb. 9, 2006

(51) Int. Cl.
*A01H 5/00* (2006.01)
*A01H 5/10* (2006.01)

(52) U.S. Cl. ..................................... 800/298
(58) Field of Classification Search .................. 800/298
See application file for complete search history.

(56) References Cited

OTHER PUBLICATIONS

Dwivedi et al. Journal of Medicinal and Aromatic Plant Sciences 21: 373-374, 1999.*

* cited by examiner

*Primary Examiner*—David H Kruse
*Assistant Examiner*—Keith O. Robinson
(74) *Attorney, Agent, or Firm*—Mark T. Skoog; Merchant & Gould P.C.

(57) ABSTRACT

Indian basil, *Ocimum basilicum,* belongs to the family of Lamiaceae. The essential oil of Indian basil extracted via hydro or steam distillation from the leaves or whole plants is used to flavor foods, dental and oral products, in fragrances, and in traditional rituals and medicines. Extracted essential oil has also been shown to contain biologically active constituents that are insecticidal, nematicidal, fungistatic or which have antimicrobial properties. The present invention relates to the development of an early, short duration, dwarf, high essential oil, methy chavicol and linalool yielding variety of Indian basil (*Ocimum basilicum*). Family—Lamiaceae) named as 'CIM-SAUMYA'. This new variety of Indian basil was developed through open pollination in the germplasm followed by half-sib progeny selection and evaluation for the yield characters of selected population for 3 years in field conditions. The new cultivar possesses better growth and vegetative growth and is able to produce higher herbage, oil and better combination of methyl chavicol and linalool yield per unit area as compared to other control genotypes.

11 Claims, 2 Drawing Sheets

SEQUENCE LISTING

<160> NUMBER OF SEQ ID NOS: 20

<210> SEQ ID NO 1
<211> LENGTH: 10
<212> TYPE: DNA
<213> ORGANISM: Artificial
<220> FEATURE:
<223> OTHER INFORMATION: Operon Primer OPA 01

<400> SEQUENCE: 1
aaatcggagc                                                          10

<210> SEQ ID NO 2
<211> LENGTH: 10
<212> TYPE: DNA
<213> ORGANISM: Artificial
<220> FEATURE:
<223> OTHER INFORMATION: Operon Primer OPA 02

<400> SEQUENCE: 2
gtcctactcg                                                          10

<210> SEQ ID NO 3
<211> LENGTH: 10
<212> TYPE: DNA
<213> ORGANISM: Artificial
<220> FEATURE:
<223> OTHER INFORMATION: Operon Primer OPA 03

<400> SEQUENCE: 3
gtccttagcg                                                          10

<210> SEQ ID NO 4
<211> LENGTH: 10
<212> TYPE: DNA
<213> ORGANISM: Artificial
<220> FEATURE:
<223> OTHER INFORMATION: Operon Primer OPA 04

<400> SEQUENCE: 4
tgcgcgatcg                                                                  10

<210> SEQ ID NO 5
<211> LENGTH: 10
<212> TYPE: DNA
<213> ORGANISM: Artificial
<220> FEATURE:
<223> OTHER INFORMATION: Operon Primer OPA 05

<400> SEQUENCE: 5
aacgtacgcg                                                                  10

<210> SEQ ID NO 6
<211> LENGTH: 10
<212> TYPE: DNA
<213> ORGANISM: Artificial
<220> FEATURE:
<223> OTHER INFORMATION: Operon Primer OPA 06

<400> SEQUENCE: 6
gcacgccgga                                                                  10

<210> SEQ ID NO 7
<211> LENGTH: 10
<212> TYPE: DNA
<213> ORGANISM: Artificial
<220> FEATURE:
<223> OTHER INFORMATION: Operon Primer OPA 07

<400> SEQUENCE: 7
caccctgcgc                                                                  10

<210> SEQ ID NO 8
<211> LENGTH: 10
<212> TYPE: DNA
<213> ORGANISM: Artificial
<220> FEATURE:
<223> OTHER INFORMATION: Operon Primer OPA 08

<400> SEQUENCE: 8
ctatcgccgc                                                                  10

<210> SEQ ID NO 9
<211> LENGTH: 10
<212> TYPE: DNA
<213> ORGANISM: Artificial
<220> FEATURE:
<223> OTHER INFORMATION: Operon Primer OPA 09

<400> SEQUENCE: 9
cgggatccgc                                                                  10

<210> SEQ ID NO 10
<211> LENGTH: 10
<212> TYPE: DNA
<213> ORGANISM: Artificial
<220> FEATURE:
<223> OTHER INFORMATION: Operon Primer OPA 10

<400> SEQUENCE: 10
gcgaattccg                                                                  10

<210> SEQ ID NO 11
<211> LENGTH: 10
<212> TYPE: DNA
<213> ORGANISM: Artificial

-continued

```
<220> FEATURE:
<223> OTHER INFORMATION: Operon Primer 11

<400> SEQUENCE: 11
ccctgcaggc                                                                10

<210> SEQ ID NO 12
<211> LENGTH: 10
<212> TYPE: DNA
<213> ORGANISM: Artificial
<220> FEATURE:
<223> OTHER INFORMATION: Operon Primer 12

<400> SEQUENCE: 12
ccaagcttgc                                                                10

<210> SEQ ID NO 13
<211> LENGTH: 10
<212> TYPE: DNA
<213> ORGANISM: Artificial
<220> FEATURE:
<223> OTHER INFORMATION: Operon Primer OPA 13

<400> SEQUENCE: 13
gtgcaatgag                                                                10

<210> SEQ ID NO 14
<211> LENGTH: 10
<212> TYPE: DNA
<213> ORGANISM: Artificial
<220> FEATURE:
<223> OTHER INFORMATION: Operon Primer OPA 14

<400> SEQUENCE: 14
aggatacgtg                                                                10

<210> SEQ ID NO 15
<211> LENGTH: 10
<212> TYPE: DNA
<213> ORGANISM: Artificial
<220> FEATURE:
<223> OTHER INFORMATION: Operon Primer OPA 15

<400> SEQUENCE: 15
aagatagcgg                                                                10

<210> SEQ ID NO 16
<211> LENGTH: 10
<212> TYPE: DNA
<213> ORGANISM: Artificial
<220> FEATURE:
<223> OTHER INFORMATION: Operon Primer OPA 16

<400> SEQUENCE: 16
ggatctgaac                                                                10

<210> SEQ ID NO 17
<211> LENGTH: 10
<212> TYPE: DNA
<213> ORGANISM: Artificial
<220> FEATURE:
<223> OTHER INFORMATION: Operon Primer OPA 17

<400> SEQUENCE: 17
ttgtctcagg                                                                10
```

```
<210> SEQ ID NO 18
<211> LENGTH: 10
<212> TYPE: DNA
<213> ORGANISM: Artificial
<220> FEATURE:
<223> OTHER INFORMATION: Operon Primer OPA 18

<400> SEQUENCE: 18
catcccgaac                                                          10

<210> SEQ ID NO 19
<211> LENGTH: 10
<212> TYPE: DNA
<213> ORGANISM: Artificial
<220> FEATURE:
<223> OTHER INFORMATION: Operon Primer OPA 19

<400> SEQUENCE: 19
ggactccacg                                                          10

<210> SEQ ID NO 20
<211> LENGTH: 10
<212> TYPE: DNA
<213> ORGANISM: Artificial
<220> FEATURE:
<223> OTHER INFORMATION: Operon Primer OPA 20

<400> SEQUENCE: 20
agcctgacgc                                                          10
```

DISTINCT TYPE CULTIVAR OF *OCIMUM BASILICUM* "CIM-SAUMYA"

FIELD OF INVENTION

Figure 1:
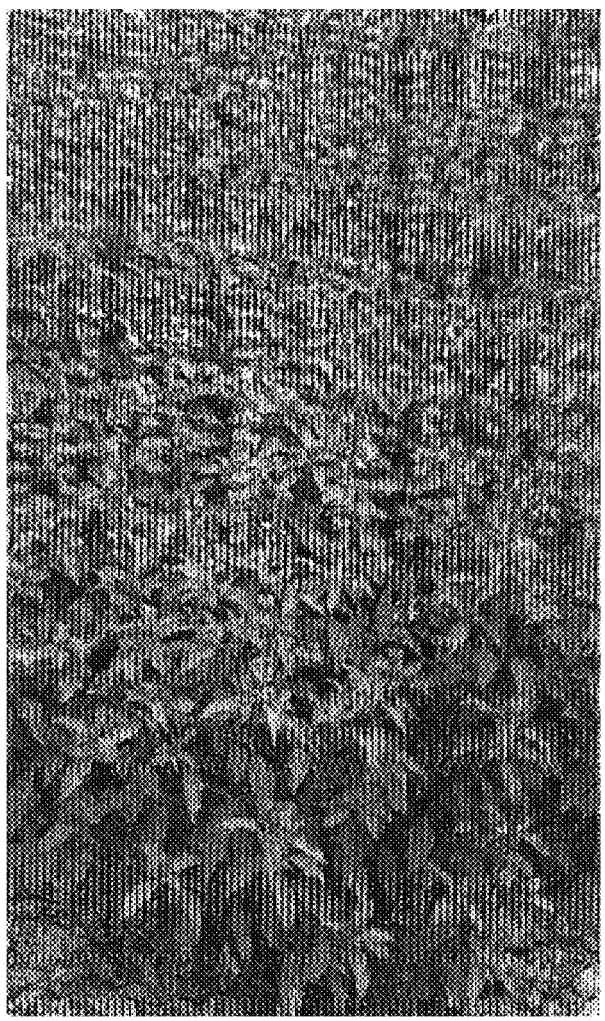

The present invention relates to the development of an early, short duration, dwarf, high essential oil, methyl chavicol and linalool yielding variety of Indian basil (*Ocimum basilicum*), Family—Lamiaceae) named as 'CIM-SAUMYA'. More particularly, the invention is related to the development of an early, short duration, dwarf, high eugenol and linalool yielding variety of Indian basil through open pollination in the germplasm followed by half-sib progeny selection and evaluation for the yield characters of selected population for 3 years in field conditions. The selected variety is high yielding and stable in subsequent generation. This invention thus relates to the seeds, plants and plant parts of CIM-SAUMYA and its components to a method of producing CIM-SAUMYA, and to a method for producing an early, short duration, high methyl chavicol and linalool using CIM-SAUMYA as a pollinator or parent.

BACKGROUND OF INVENTION

Indian basil, *Ocimum basilicum*, belongs to the family of Lamiaceae. The essential oil of Indian basil extracted via hydro or steam distillation from the leaves or whole plants used to flavour foods, dental and oral products, in fragrances, and in traditional rituals and medicines. Extracted essential oil has also been shown to contain biologically active constituents that are insecticidal, nematicidal, fungistatic or which have antimicrobial properties.

Keeping in mind the importance of Indian basil, the need for developing a better plant type having an early, short duration, dwarf, high essential oil yield characters combined with consistent high yield of methyl chavicol and linalool in the essential oil in all around the year was felt and planned breeding and selection process was undertaken at the farm of CIMAP, Lucknow to develop the variety CIM-SAUMYA.

OBJECTS OF THE INVENTION

The main object of the present invention is to develop a novel variety of Indian basil *Ocimum basilicum* named as CIM-SAUMYA having an early, short duration, dwarf, high essential oil yield characters combined with consistent high yield of methyl chavicol and linalool in the essential oil.

Another object of the present invention is to develop an early, short duration, dwarf, high eugenol and linalool yielding variety of Indian basil through open pollination in the germplasm followed by half-sib progeny selection and evaluation for the yield of characters of selected population.

A further object of the present invention is to develop seeds, plants and plant parts of CIM-SAUMYA.

DETAILED DESCRIPTION

Half-sib progeny selections can be used to improve populations of either self- or cross-pollinating crops. A genetically variable population of heterozygo as individuals is either identified or created by intercrossing several different parents. The best plants are selected based on individual superiority, outstanding progeny, or excellent combining ability. The selected plants are intercrossed to produce a new population in which further cycles of selection are continued.

Morphological description of the genus *Ocimum*:
(i) Calyx-tube in bilipped, the posterior lobe being larger
(ii) Corolla-tube is short and bilipped, posterior lip is four-lobed and anterior lobe is flat
(iii) Ovary is tetra locular
(iv) Stigma is bifid
(v) Plant are aromatic
(vi) Other related species are: *Salvia officinalis, Coleous blumei, Leucas aspera*, etc.

In the present invention which was carried out under genetic improvement programme of Indian basil (*Ocimum basilicum*), the diverse germplasm/genetic stocks of Indian basil were collected from Utter Pradesh, Bihar, Madhya Pradesh, Orissa, Uttranchal, Gujarat, Maharashtra, Jammu and Kashmir, West Bangal states of India. The germplasm were grown in plots of 1.0 m×10.0 m size plots with 50 cm×50 cm spacing randomly. The seeds collected from individual plants were germinated in the next season (May) and transferred to the main field for evaluation (in June). Randomly 25 plants were evaluated for better plant types with high herb, oil yield of better quality, out of which 10 plants were selected. The seeds from these plants were planted in the next season. The same process was repeated in the next year and ultimately 10-plant types were taken for preliminary evaluation.

Ten promising genetic stocks along with checks (controls) STA-1 and existing variety Vikarsudha were evaluated in Initial Evaluation Trial (IET). The evaluations were carried out in randomised block design (RBD) with two replications in 0.50 m$^2$ plots for each treatment during year 2000-2001. Two best performing selections IB-31 and OB-4 of I.E.T. and two checks STA-1 and Vikarsudha were evaluated in Bench Scale Trial (BST). The evaluations were carried out in randomised block design (RBD) with four replications in 12.24 m2 plots for each treatment during year 2001-2002. Finally, two most promising selections IB-31 and OB-4 along with two checks STA-1 and Vikarsudha were evaluated in Pilot Scale Trial (PST) in 2002-2003 (36.72 m$^2$ for each treatment) (Table 1). On an average, the elite strain IB-31 registered its superiority over all other selections including checks STA-1 and Vikarsudha for essential oil yield of better quality per unit area (Table 2). The elite strain was named as variety CIM-SAUMYA.

Best temperature for the crop growth was found to be 25-45° C. and medium dry to humid climate.

During screening and experimentation individual strains were maintained in seed plots with an isolation distance of 500 m$^2$ and seeds obtained from these seed plots were used in growing the plants for evaluation. During the evaluation trials 10 plants from each strains were evaluated through profiling the population DNA and comparing among each other for maintenance of purity and stability through generations. The plants when grown in isolation as mentioned are self pollinated and maintain the stability and purity as observed from the morphological, essential oil and DNA profiles.

The strain IB-31 (subsequently named as CIM-SAUMYA) consistently showed high oil content in BST and PST. The herb yield was estimated to be 290 quintals per hectare. The total oil yield was 197.20 kilogram per hectare. All the yields (yield of herb and oil) were higher than all other strains taken for comparison. The variety CIM-SAUMYA produced higher and better methyl chavicol and linalool in combination in the essential oil compared to the control varieties.

BRIEF DESCRIPTION OF THE ACCOMPANYING DRAWINGS

Figure 2:
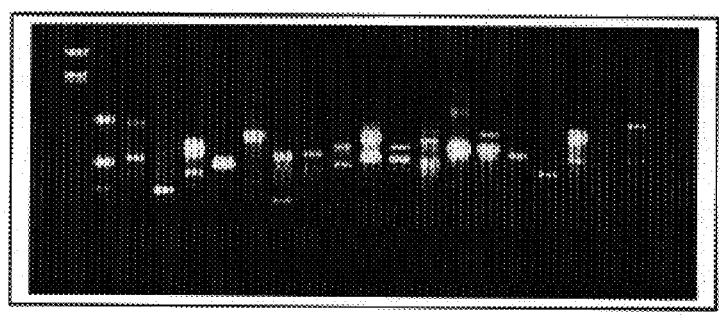

FIG. 1 shows the plant of CIM-SAUMYA;
FIG. 2 shows the unique RAPD profile of the plant CIM-SAUMYA
Samples used in lanes 2 to 21 of RAPD as shown in FIG. 2: The sequences of the primers OPA01 to OPA20 were AAATCGGAGC, GTCCTACTCG, GTCCTTAGCG, TGCGCGATCG, AACGTACGCG, GCACGCCGGA, CACCCTGCGC, CTATCGCCGC, CGGGATCCGC, GCGAATTCCG, CCCTGCAGGC, CCAAGCTTGC, GTGCAATGAG, AGGATACGTG, AAGATAGCGG, GGATCTGAAC, TTGTCTCAGG, CATCCCGAAC, GGACTCCACG, AGCCTGACGC, SEQ ID NO: 1-20, respectively. The primers AAATCGGAGC, TGCGCGATCG, AACGTACGCG, CGGGATCCGC, GCGAATTCCG, CCCTGCAGGC, CCAAGCTTGC, AAGATAGCGG, GGATCTGAAC, TTGTCTCAGG, GGACTCCACG, and CACCCTGCGC were used to develop the unique fingerprint pattern of the variety.

The *Ocimum basilicum* cultivar named 'CIM-SAUMYA' has been deposited with the National Collection of Industrial and Marine Bacteria (NCIMB-UK) with the accession number NCIMB 41414. This deposit was made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of the deposit. The deposit will be made available by NCIMB-UK under the terms of the Budapest Treaty, and subject to an agreement between NCIMB-UK and the Central Institute of Medicinal and Aromatic Plants (India), which assures permanent and unrestricted availability of the progeny of the culture of the deposit to the public upon issuance of the pertinent U.S. patent or upon laying open to the public any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 37 C.F.R. § 1.14, with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

When the uniform plant population of CIM-SAUMYA is grown in isolation with minimum isolation distance of 500 m from other genotypes of *Ocimum basilicum*, outcrossing from undesirable genotypes does not take place. Instead the population purity is being maintained through restricting pollination within the population components maintain allelic balance within the population in nature of equilibrium. In the present invention the purity of the plant variety was maintained by growing the plant population with an isolation distance of 500 m from any other genotypes of *Ocimum basilicum*. The stability of the plant population was checked through pooled DNA profiling using 20 OPA (OPA01 to 20) primers (Procured from Operon Technologies, USA) in subsequent generations and found to be uniform without variation. These primers were also used to develop the unique fingerprint pattern of the variety and the pattern was found to be consistent for three generations.

TABLE 1

Mean performance of promising strains in different yield trials for herb and oil yield in Indian basil (*Ocimum basilicum*)

| | | BST (RBD, reps 4, plot size-12.24 sqm) | | | PST (plot size-36.72 sqm) | | | | | |
|---|---|---|---|---|---|---|---|---|---|---|
| | | Herb yield (kg/plot) | Oil content (%) | Oil yield (g/plot) | Mean herb yield (kg/plot) | Oil content (%) | | Oil yield | Herb yield (ql/ha) | Oil yield (kg/ha) |
| S. No | Entries | Fresh herb | Fresh leaves | Fresh leaves | Fresh leaves | Fresh leaves | Dry leaves | (gm/plot) Fresh leaves | Fresh leaves | Fresh leaves |
| 1. | IB 31 | 34.92 | 0.67 | 235.28 | 106.49 | 0.68 | 0.99 | 724.13 | 290.00 | 197.20 |
| 2. | OB-4 | 54.49 | 0.17 | 94.69 | 120.40 | 0.18 | 0.65 | 216.72 | 327.89 | 59.02 |
| 3. | Vikarsudha | 39.63 | 0.48 | 190.16 | 123.01 | 0.50 | 0.90 | 615.05 | 335.00 | 167.50 |
| 4. | STA-1 | 12.90 | 0.10 | 10.49 | 38.56 | 0.10 | 0.20 | 38.56 | 105.02 | 10.52 |
| | SE m | 0.32 | 0.08 | 2.89 | | | | | | |
| | CD $_{(5\%)}$ | 1.03 | 0.03 | 9.25 | — | — | — | — | — | — |
| | CD $_{(1\%)}$ | 1.48 | 0.04 | 13.28 | — | — | — | — | — | — |

TABLE 2

Oil composition of variety CIM-SAUMYA and other varieties/check of Indian-basil

| S. No. | Constituents in oil | CIM-SAUMYA | OB 4 | Vikarsudha | STA-1 |
|---|---|---|---|---|---|
| 1. | Methyl chavicol | 62.54 | 55.74 | 78.74 | 0.38 |
| 2. | α-pinene | 0.06 | 0.16 | 0.14 | 1.49 |
| 3. | Linalool | 24.61 | 0.76 | 0.16 | 3.94 |
| 4. | Limonene | 0.06 | 0.15 | 0.11 | 0.70 |
| 5. | β-caryophyllene | 1.32 | 0.82 | 1.86 | 3.62 |
| 6. | Eugenol | 0.86 | 0.11 | 0.62 | 5.75 |
| 7. | β-myrecene | 0.01 | 0.31 | 0.30 | 1.38 |
| 8. | β-elemene | 4.40 | 7.20 | 11.38 | 27.08 |
| 9. | Sabinene | 0.16 | 0.12 | 0.12 | 0.46 |
| 10. | Germacrene-D | 0.01 | 0.45 | 1.07 | 10.85 |
| 11. | Total peaks | 56 | 28 | 42 | 60 |

FIG. 1 shows the plants of the present invention. The morphological characteristics of the plants can be clearly seen from this figure.

Taxonomic Description of the *Ocimum basilicum* Plant 'CIM-SAUMYA'
1. Genus: *Ocimum*
2. Species: *basilicum*
3. Family: Lamiaceae
4. Common name: Common basil
5. Plant height: 70.33 cm in 90 days
6. Plant canopy: 60 cm×70 cm 7. Growth habit: Erect sturdy main stem, profuse synchronous branching.
8. Stem color: Stem color: Green (146D), purple pigmentation at the time of maturity (79D)
9. Stem diameter: 0.6 cm
10. Branch number: 17
11. Petiole color: purple (79C)
12. Petiole length: 1.8 cm
13. Petiole trichomes: 44
14. Leaf numbers: 400-500
15. Leaf shape: Oblong to ob-lanceolate
16. Leaf apex: Sub-acute to acuminate
17. Leaf pubescence: stout
18. Leaf size: Moderately broad
19. Leaf angle: 22°
20. Leaf venation: Pinnate
21. Leaf color: Yellow green (146C) both upper and lower surface
22. Leaf texture: Chartaceous
23. Leaf surface: Minute hairs above, hirsute below and nevers
24. Leaf tip: Sub-acute to acuminate
25. Leaf petiole length: 1.8 cm
26. Leaf: stem ratio (w/w): 0.84
27. Leaf area: 10.8 cm$^2$ (Average of full branch)
28. Leaf moisture content: 79.92%
29. Leaf margin: Serrate
30. Leaf base: Obtuse
31. Leaf length: 2.93 cm
32. Leaf width: 2.10 cm
33. Flower inflorescence: Indefinite racemose
34. Number of flowers/plant: 10-15
35. Oil content in the dry leaf (%): 0.95 to 0.99
36. Oil quality:
    Methyl chavicol (%): 62.54-65.00
    Linalool (%): 24.61-25.00
    Eugenol (%): 0.86 to 0.90
37. Herbage (Quintal per hectare): Fresh herb: 290.00
38. Colour early stage light green (138A)
39. Sepal color: Green (146D)
40. Sepal pubescence: hairy
41. Sepal lobe shape: posterior lip larger, anterior lip consist of 4-lobes
42. Sepal length: 5 mm
43. Petal color: Violet white flower (84C)
44. Petal size: small
45. Petal length: 8 mm
46. Petal width: 2 mm
47. Petal margin: entire
48. Flower diameter: 4-6 mm
49. Corolla tube length: 3 mm
50. Corona tube diameter: 1.00-1.5 mm
51. Corona color: violet white (84C)
52. Location of notch on the petal: lower part
53. Style length: 6.5 mm
54. Anther length: 0.5 mm
55. Anther width: 0.4-0.5 mm
56. Anthers: dithecous, versatile, introse, violet white (84C)
57. Pollen size: microscopic
58. Pollen fertility: 85-90%
59. Pollen shape round
60. Pollen fertility: 85-90%
61. Stigma: superior, bifid, un feathery, vilot white color (84C),
62. Ovule: violet white (84C)
63. Ovary: size small, purple
64. Siliqua color: green
65. Siliqua tip: notched
66. Siliqua orientation:: verticillaster
67. Siliqua size: small
68. Siliqua length: 0.1 mm
69. Siliqua diameter: 0.2 mm
70. Seed/siliqua: 1
71. Seed size: 0.08 mm
72. Seed shape: oblong
73. Seed color: black
74. 100 seed weight: 0.12 gm
75. Seed surface: smooth
76. Seed germinability: 85-90%

The color codes are in accordance with the R.H.S. color chart published by The Royal Horticulture Society, 80 Vincent Square, London SWIP2PE, 1995.

Time period for growing after planting: 90 days, Selection for three years: In the present invention which was carried out under genetic improvement programme of Indian basil (*Ocimum basilicum*), the diverse germplasm/genetic stocks of Indian basil were collected from Utter Pradesh, Bihar, Madhya Pradesh, Orissa, Uttranchal, Gujarat, Maharashtra, Jammu and Kashmir, West Bangal states of India. The germplasm were grown in plots of 1.0 m×10.0 m size plots with 50 cm×50 cm spacing randomly. The seeds collected from individual plants were germinated in the next season (May) and transferred to the main field for evaluation (in June). Randomly 25 plants were evaluated for better plant types with high herb, oil yield of better quality, out of which 10 plants were selected. The seeds from these plants were planted in the next season. The same process was repeated in the next year and ultimately 10-plant types were taken for preliminary evaluation.

Evaluation trials: Ten promising genetic stocks along with checks (controls) STA-1 and existing variety Vikarsudha were evaluated in Initial Evaluation Trial (IET). The evaluations were carried out in randomized block design (RBD) with two replications in 0.50 m$^2$ plots for each treatment during year 2000-2001. Two best performing selections IB-31 and OB-4 of I.E.T. and two checks STA-1 and Vikarsudha were evaluated in Bench Scale Trial (BST). The evaluations were carried out in randomised block design (RBD) with four replications in 12.24 m$^2$ for each treatment during year 2001-2002. Finally, two most promising selections IB-31 and OB-4 along with two checks STA-1 and Vikarsudha were evaluated in Pilot Scale Trial (PST) in 2002-2003 (36.72 m$^2$ for each treatment). On an average, the elite strain IB-31 registered its superiority over all other selections including checks STA-1 and Vikarsudha for essential oil yield of better quality per unit area. The elite strain was named as variety CIM-SAUMYA.

The stability of the plant population was checked through pooled DNA profiling using 20 OPA (OPA01 to 20) primers (Procured from Operon Technologies, USA) in subsequent generations and found to be uniform without variation. These primers were also used to develop the unique fingerprint pattern of the variety and the pattern was found to be consistent for three generations. Samples used in lanes 2 to 21 of RAPD: The sequences of the primers OPA01 to OPA20 were AAATCGGAGC, GTCCTACTCG, GTCCTTAGCG, TGCGCGATCG, AACGTACGCG, GCACGCCGGA, CACCCTGCGC, CTATCGCCGC, CGGGATCCGC, GCGAATTCCG, CCCTGCAGGC, CCAAGCTTGC, GTGCAATGAG, AGGATACGTG, AAGATAGCGG, GGATCTGAAC, TTGTCTCAGG, CTACCCGAAC, GGACTCCACG, AGCCTGACGC, respectively. The primers AAATCGGAGC, TGCGCGATCG, AACGTACGCG, CGGGATCCGC, GCGAATTCCG, CCCTGCAGGC, CCAAGCTTGC, AAGATAGCGG, GGATCTGAAC, TTGTCTCAGG, GGACTCCACG, and CACCCTGCGC (SEQ ID NO:1-20, respectively) were used to develop the unique fingerprint pattern of the variety.

Comparison of character of CIM-SAUMYA with the checks (STA-1 and Vikarsudha)

| Attributes | Elite strain CIM-SAUMYA (IB 31) | Checks STA-1 | Vikarsudha |
|---|---|---|---|
| Plant height (cm) | Dwarf (70.33) | Tall (80) | Tall (97.67) |
| Days to flowering (50%) | 75-80 | 110-120 | 90-100 |
| Crop duration | Short/early | long/late | long/late |
| Growth habit | Semi closed | Open | Open |
| No. of branches/plant | 17.33 | 12.67 | 12.67 |
| Length of leave (cm) | 2.93 | 4.63 | 4.60 |

-continued

Comparison of character of CIM-SAUMYA with the checks (STA-1 and Vikarsudha)

| Attributes | Elite strain CIM-SAUMYA (IB 31) | Checks STA-1 | Vikarsudha |
|---|---|---|---|
| Width of leave (cm) | 1.73 | 2.83 | 2.83 |
| Fresh herb yield (ql/ha) | 290.00 | 105.02 | 335.00 |
| Oil content (%) in fresh herb | 0.68 | 0.10 | 0.50 |
| Oil content in dry herb | 0.99 | 0.20 | 0.90 |
| Oil yield (Kg/ha) | 197.20 | 10.52 | 167.50 |
| Colour of stem | Light brown | Brown | Dark brown |
| Colour of leaves | Yellow green | Dark red/purple | Green |
| Methyl chavicol (%) | 62.54 | 0.38 | 78.74 |
| Linalool (%) | 24.61 | 3.94 | 0.16 |

The invention claimed is:

1. An *Ocimum basilicum* cultivar obtained from seed deposited with the NCIMB-UK having accession number MCIMB 41414 and named 'CIM-SAUMYA', belonging to the family Laminaceae.

2. The cultivar of claim 1, wherein the cultivar is about 10 to 30 cm shorter than tall checks.

3. The cultivar of claim 1, wherein the cultivar produces said essential oil yield in an amount of at least about 197.20 kg/hectare.

4. The cultivar of claim 1, wherein the cultivar produces herbage yield of 290.00 quintals per hectare.

5. The cultivar of claim 1, wherein the cultivar produces a 60 cm×70 cm canopy area and a height of at least 70.33 cm in a maximum of 90 days.

6. The cultivar of claim 1, wherein the 50% of the plants produce flowers 75-80 days after planting.

7. The cultivar of claim 1, wherein the cultivar produces yellow green leaves characterized by color 146C of the RHS color chart and violet white flowers characterized by color 84C of the RHS color chart.

8. The cultivar of claim 1, wherein the cultivar has an early and short crop duration compared to conventional cultivars.

9. The cultivar of claim 1, wherein the cultivar yields about 235 grams of oil from the fresh leaves of about 12 square meters of cultivar grown for 90 days.

10. A seed of *Ocimum basilicum* deposited at the NCIMB-UK having accession number NCIMB 41414.

11. The cultivar of claim 1 having the following characteristics:
  a. a distinct random amplified polymorphic DNA (RAPD) molecular profile using primers having the sequence of SEQ ID NO: 1, 3, 4, 7, 9, 10, 11, 12, 15, 16, 17 and 19 that distinguish the cultivar from other cultivars; and
  b. an essential oil comprising about 62.54% methyl chavicol, about 24.61% linalool, about 0.06% α-pinene, about 0.06% Limonene, about 1.32% β-caryophyllene, about 0.86% Eugenol, about 0.01% β-myrecene, about 4.40% β-elemene, about 0.16% Sabinene and about 0.01% Germacrene-D.

* * * * *